(12) United States Patent
Genin et al.

(10) Patent No.: US 11,813,322 B2
(45) Date of Patent: Nov. 14, 2023

(54) STABILIZED LIQUID LIVE VACCINE

(71) Applicant: Boehringer Ingelheim Animal Health USA Inc., Duluth, GA (US)

(72) Inventors: Noel Yves Henri Jean Genin, Saint Genis les Ollieres (FR); David Pierre Corneille, Fareins (FR); Bradley Eddy, St. Joseph, MO (US)

( * ) Notice: Subject to any disclaimer, the term of this patent is extended or adjusted under 35 U.S.C. 154(b) by 159 days.

(21) Appl. No.: 16/893,706

(22) Filed: Jun. 5, 2020

(65) Prior Publication Data

US 2020/0384101 A1 Dec. 10, 2020

Related U.S. Application Data

(60) Provisional application No. 62/859,491, filed on Jun. 10, 2019.

(51) Int. Cl.
| | | |
|---|---|---|
| *A61K 39/155* | (2006.01) | |
| *A61K 47/18* | (2017.01) | |
| *A61K 47/26* | (2006.01) | |
| *A61K 47/42* | (2017.01) | |

(52) U.S. Cl.
CPC .......... *A61K 39/155* (2013.01); *A61K 47/183* (2013.01); *A61K 47/26* (2013.01); *A61K 47/42* (2013.01)

(58) Field of Classification Search
None
See application file for complete search history.

(56) References Cited

U.S. PATENT DOCUMENTS

2015/0098967 A1\* 4/2015 Vadrevu .................. A61K 9/08
424/215.1

FOREIGN PATENT DOCUMENTS

| EP | 0028563 A1 | 5/1981 |
|---|---|---|
| WO | 2015121463 A2 | 8/2015 |

OTHER PUBLICATIONS

Mariner et al., Vaccine 35: 3773-3779 (Year: 2017).\*
White et al., "Development of a stable liquid formulation of live attenuated influenza vaccine", Vaccine, vol. 34, Issue 32, 2016, pp. 3676-3683.

\* cited by examiner

*Primary Examiner* — Shanon A. Foley
*Assistant Examiner* — Myron G Hill
(74) *Attorney, Agent, or Firm* — Steffan Finnegan

(57) ABSTRACT

The present invention relates generally to the fields of immunology and vaccine technology. More specifically, the present invention relates to stabilized liquid immunogenic compositions and vaccines having a live attenuated viral antigen, and methods of using the same. The live attenuated viral antigen can be a live peste des petits ruminants (PPR) virus.

17 Claims, 1 Drawing Sheet

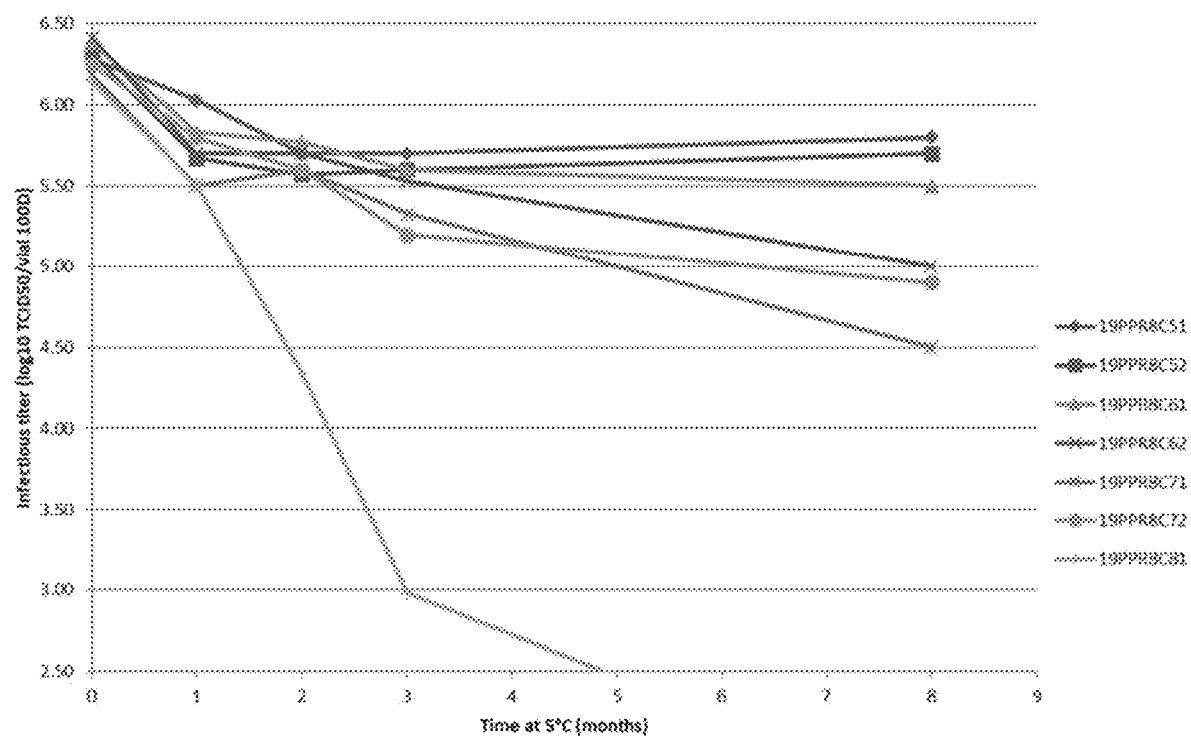

STABILIZED LIQUID LIVE VACCINE

CROSS-REFERENCE TO RELATED APPLICATIONS

This application claims priority to U.S. provisional application 62/859,491 filed on Jun. 10, 2019, the entire contents of which are hereby incorporated by reference herein.

RELATED APPLICATIONS AND INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a liquid vaccine formulation with one or more stabilizers and methods for making and using the same.

BACKGROUND OF THE INVENTION

Immunogenic compositions and vaccine compositions comprising biological ingredients, such as viruses, bacteria, parasites, fungi, proteins, polypeptides, glycoproteins, and especially, attenuated live microorganisms, are markedly sensitive to the conditions by which they are prepared, formulated and stored. Many viruses are sensitive to pH, osmolarity, and oxidation, and thus subject to degradation of the virus in a liquid formulation.

Most live attenuated virus vaccines are lyophilized, i.e., freeze-dried, prior to their long-term storage. The live attenuated virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized vaccines that comprise live attenuated viruses are stored with augmented titers. However, such increased titers can lead to significant adverse events should the lyophilization process actually lead to less loss of activity than anticipated. Therefore, great care is required to formulate a vaccine to contain a virus titer that is not only safely below the amount that leads to adverse events, but that also maintains sufficient efficacy in view of the virus titer loss due to lyophilisation and subsequent storage.

So far, live vaccines are mostly freeze-dried. This process is good for the stability, but has some drawbacks: 1) drawbacks due to the process itself: limited throughput due to freeze-drying (work under high vacuum, long cycle times), which is important to capex costs; 2) drawbacks due to the final use of vaccine in the field: need a sterile diluent to rehydrate the freeze-dried cake, and therefore need to manipulate two bottles in the field (vaccine and diluent bottles), leading to an increased cogs. Getting rid of the diluent bottle would reduce the cogs and bring convenience to the customer, especially for the chicken, swine, and ruminant industries where the ease of use and the cost are important parameters.

A liquid vaccine formulation would fix most of the drawbacks of freeze-dried vaccines, including a reduction of capex and cost of goods, drastic improvement of throughput, and improvement of customer convenience. To realize viable liquid vaccine formulations, it is desirable to have a stabilizer that effectively protects the integrity of the active ingredients (e.g., live virus) during manufacture, storage, and transport. Thus, there is a need for new, stabilized liquid vaccines comprising live attenuated virus and which can reliably retain their virus titers at a safe and efficacious level.

SUMMARY OF THE INVENTION

To overcome the deficiencies of current vaccines, the present invention provides novel liquid immunogenic compositions and vaccines comprising a stabilized live attenuated virus. The present invention also provides methods of administering such immunogenic compositions and vaccines to an animal. The present invention further provides methods of immunizing an animal against a disease through administering a vaccine of the present invention.

BRIEF DESCRIPTION OF THE DRAWINGS

FIG. 1 graphically presents stability results at 1, 2, 3, and 8 months at 5° C.

DETAILED DESCRIPTION OF THE INVENTION

Throughout this disclosure, the percent (%) w/v of any component is provided as the weight (w) of the component to the volume (v) of the immunogenic composition or vaccine.

A "subject" in the context of the present invention can be a mammal; advantageously a ruminant such as a bovine (cattle), an ovine (sheep), or a caprine (goat).

An "antigen" is a substance that is recognized by the immune system and induces an immune response. The antigen may comprise a whole organism, killed, attenuated, or live. The antigen may comprise a live attenuated pathogen, such as a live attenuated virus.

A "pathogen" refers to a specific causative agent of disease, such as a virus.

An "immunogenic composition" refers to any composition that, after administration into a subject, elicits an immune response targeted against an antigen of interest.

A "vaccine" refers to a composition that, after administration into a subject, elicits a protective immune response targeted against an antigen of interest.

A "live attenuated" pathogen, such as a live attenuated virus, refers to a pathogen having a reduced virulence but still remaining viable (e.g., attenuation takes an infectious agent and alters it so that it becomes harmless or less virulent). It is generally agreed that immunogenic compositions or vaccine compositions based on live attenuated microorganisms have the ability to induce a highly effective type of immune response. Such immunogenic compositions or vaccine compositions have the advantage that, once an animal host has been immunized, entry of the pathogen into the host induces an accelerated recall of earlier, cell-mediated or humoral immunity, which is able to control the further growth of the organism before the infection can assume clinically significant proportions.

The term "stable" as used herein is understood to mean that the antigen used in the immunogenic compositions and vaccines of the present disclosure will sufficiently maintain its immunogenic capacity for the required shelf life duration of the immunogenic compositions and vaccines. In embodiments, a stable immunogenic composition or vaccine will retain at least 20%, 25% 30%, 35%, 40%, 45%, 50%, 55%, 60%, 65%, 70%, 75%, 80%, 85%, 90%, 95% or greater of its immunogenic capacity or original vaccine titer after 1, 2, 3, 4, 5, 6, 7, 8, 19, 10, 11, 12, 15, 18, 24, 30, or 36 months.

A "stabilized liquid" immunogenic composition or vaccine is an immunogenic composition or vaccine maintained as a liquid that remains efficacious for at least one year when stored at or below 7° C. (e.g., a standard refrigerator temperature will be in the 0° C.-7° C. range) In embodiments, a liquid stabilized immunogenic composition or vaccine remains efficacious when stored at or below 7° C. for at least 1, 1.5, 2, 2.5, or 3 years.

The term "stabilizer" as used herein is a chemical substance or a mixture of chemicals that stabilize antigenic material during lower temperature storage. The stabilizer is typically admixed in the immunogenic composition or vaccine in an amount sufficient to stabilize the antigen for a period of time. Stabilizers can include monosaccharides (e.g., sorbitol) or disaccharides (e.g., sucrose, lactose, or maltose). Stabilizers can also include amino acids (e.g., alanine, arginine, aspartic acid, cystine, glutamic acid, glycine, histidine, hydroxy proline, isoleucine, leucine, lysine, methionine, phenyl alanine, proline, serine, threonine, tyrosine, and valine) and salts thereof (e.g., L-arginine hydrochloride salt, glutamic acid alkali metal salt (e.g., monosodium glutamate and monopotassium glutamate)); proteins and salts thereof (e.g., protein hydrolysate, bovine protein, mouse serum protein, calf serum protein, yeast protein, chicken protein, egg protein, albumin (e.g., bovine albumin, ovalbumin), gelatin, and hydrolysed gelatin).

The term "veterinarily acceptable" is used adjectivally to mean that the modified noun is appropriate for use in a veterinary product. When it is used, for example, to describe an excipient in a veterinary vaccine, it characterizes the excipient as being compatible with the other ingredients of the vaccine and not disadvantageously deleterious to the intended recipient.

The term "diluent" refers to a liquid that is mixed with other components of the immunogenic composition or vaccine to provide a final form for administration. Examples of veterinarily acceptable diluents include sterile liquids such as water, oil, aqueous saline solutions, and aqueous sugar solutions (e.g. dextrose solution, glycerol solution).

The term "adjuvant" refers to a substance that boosts an immune response to antigen. An adjuvant is in general not required for an immunological response to occur, but rather favors or amplifies this response.

The term "sugar additive" refers to a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol).

The term "reducing monosaccharide" refers to a saccharide that is able to donate electrons, and thus, able to reduce another compound during oxidation-reduction reactions. Generally, a reducing monosaccharide has aldehyde or ketone groups in its structure. Colorimetric tests are available to identify reducing sugars, such as the Fehling's reagent test (i.e. a solution containing the bistartratocuprate (II) anion, $[Cu(C_4H_4O_6)_2]^{4-}$), which yields a color change from deep blue to red as the copper ion reagent is reduced to the copper metal in presence of a reducing sugar. Reducing monosaccharides can provide protection for proteins and live attenuated pathogens in a composition (e.g., by maintaining cohesion of the biological structure).

The term "non-reducing sugar" refers to a sugar additive that, in a basic aqueous medium, does not generate any compounds containing an aldehyde group. Examples of non-reducing sugars include sucrose and trehalose.

The present disclosure provides liquid immunogenic compositions and vaccines comprising an attenuated live pathogen and a stabilizer. The liquid immunogenic compositions and vaccines may be in a ready to use form (e.g., ready for administration).

In embodiments, the attenuated live pathogen is a virus. The liquid immunogenic compositions and vaccines can include viruses of any type (e.g., enveloped, non-enveloped, single-stranded RNA genome, single-stranded DNA genome, or double-stranded DNA genome). In embodiments, the attenuated live virus is selected from an attenuated live peste des petits ruminants (PPR) virus, African horse sickness virus, rindepest virus, foot-and-mouth disease virus, African swine fever virus, and bluetongue virus. In embodiments, the attenuated live virus is a PPR virus.

In embodiments, the attenuated live pathogen is about 1% w/v to about 5% w/v of the immunogenic composition or vaccine. In embodiments, the attenuated live pathogen is about 3% w/v of the immunogenic composition or vaccine.

In embodiments, the immunogenic compositions and vaccines comprise attenuated live pathogen in an amount between 3 log 10 TCID50/ml to 9 log 10 TCID50/ml, between 4 log 10 TCID50/ml to 8 log 10 TCID50/ml, between 4 log 10 TCID50/ml to 7 log 10 TCID50/ml, or between 5 log 10 TCID50/ml to 6 log 10 TCID50/ml. In embodiments, the immunogenic compositions and vaccines comprise attenuated live pathogen in an amount of about 4 log 10 TCID50/ml, of about 4.5 log 10 TCID50/ml, of about 5 log 10 TCID50/ml, of about 5.5 log 10 TCID50/ml, of about 6 log 10 TCID50/ml, of about 6.5 log 10 TCID50/ml, or of about 7 log 10 TCID50/ml.

In embodiments, the stabilizer comprises a non-reducing sugar, such as sucrose, trehalose, raffinose, stachyose, and/or verbascose. In embodiments, the stabilizer comprises the non-reducing sugar sucrose. In embodiments, the sucrose is E-sucrose or E-saccharose. The "E" designation indicates that the substance is permitted to be used as a food additive for use in the European Union and the European Free Trade Association. In particular, the sucrose is a purified and crystallized sucrose with a polarization not less than 99.7° Z. However, regular table sucrose is contemplated to be effective in the present invention. The stabilizer may comprise about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, or about 1% to about 20% w/v of the non-reducing sugar. In embodiments, the stabilizer may comprise about 10% w/v of the non-reducing sugar (e.g., sucrose).

In embodiments, the stabilizer comprises lactalbumin, which is the albumin contained in milk and obtained from whey. In embodiments, the stabilizer comprises lactalbumin hydrolysate, which is the enzymatically hydrolyzed protein portion of milk whey. In embodiments, the lactalbumin and/or lactalbumin hydrolysate are irradiated. In embodiments, the stabilizer may comprise about 0.5%, about 0.6%, about 0.7%, about 0.8%, about 0.9%, about 1%, about 2%, about 3%, about 4%, about 5%, about 6%, about 7%, about 8%, about 9%, about 10%, or about 0.5% to about 10% w/v of the lactalbumin and/or lactalbumin hydrolysate. In embodiments, the stabilizer may comprise about 5% w/v of the lactalbumin or lactalbumin hydrolysate.

In embodiments, the stabilizer comprises monosodium glutamate (the sodium salt of glutamic acid) and/or monosodium glutamate monohydrate. In embodiments, the stabilizer comprises E-monosodium glutamate and/or E-monosodium glutamate monohydrate. The "E" designation indicates that the substance is permitted to be used as a food additive for use in the European Union and the European Free Trade Association. In embodiments, the stabilizer may comprise about 0.5%, about 0.6%, about 0.7%, about 0.8%, about 0.9%, about 1%, about 1.1%, about 1.2%, about 1.21%, about 1.22%, about 1.23%, about 1.24%, about 1.25%, about 1.26%, about 1.27%, about 1.28%, about 1.29%, about 1.3%, about 1.4%, about 1.5%, about 1.6%, about 1.7%, about 1.8%, about 1.9%, about 2%, about 3%, about 4%, about 5%, or about 0.5% to about 5% w/v of the monosodium glutamate component. In embodiments, the stabilizer may comprise about 1.25% w/v of the monosodium glutamate component.

In embodiments, the stabilizer comprises a reducing sugar, such as a reducing monosaccharide, lactose, or maltose. In embodiments, the stabilizer comprises maltose. In embodiments, the stabilizer comprises a reducing monosaccharide such as glucose, galactose, fructose, mannose, and/or sorbose. In embodiments, the stabilizer comprises about 10%, about 15%, about 20%, about 25%, about 30%, about 35%, about 40%, about 45%, about 50%, about 55%, about 60%, about 65%, about 70%, about 75%, about 80%, or about 10% to about 80% w/v of the non-reducing sugar. In embodiments, the stabilizer comprises about 40% w/v of the reducing sugar (e.g., maltose).

In embodiments, the stabilizer comprises E-sucrose, irradiated lactalbumin hydrolysate, E-glutamate sodium, and/or maltose. In embodiments, the E-sucrose is about 10% w/v of the stabilizer, the irradiated lactalbumin hydrolysate is about 5% w/v of the stabilizer, the E-glutamate sodium is about 1.25% w/v of the stabilizer, and the maltose is about 40% w/v of the stabilizer.

In embodiments, the liquid immunogenic compositions and vaccines comprise a veterinarily acceptable diluent. Examples of veterinarily acceptable diluents include sterile liquids such as water, oil, aqueous saline solutions, and aqueous sugar solutions (e.g. dextrose solution, glycerol solution).

In embodiments, the liquid immunogenic compositions and vaccines have an isotonic concentration. In embodiments, the liquid immunogenic compositions and vaccines have an isotonic concentration in the range of about 100-600 mOsm, about 250-450 mOsm, or about 330 mOsm.

In embodiments, the liquid immunogenic compositions and vaccines have a pH range of about 6.0 to about 8.0, or about 6.5 to about 7.5. In embodiments, the liquid immunogenic compositions and vaccines have a pH of about 7.1. The pH may be adjusted by any suitable acid or base, such as sodium hydroxide. In embodiments, the liquid immunogenic compositions and vaccine comprise a buffer to help maintain the pH of the liquid immunogenic compositions and vaccines. Examples of suitable buffers include potassium phosphate, sodium phosphate, Tris, Tris-Histidine, BIS-Tris, BIS-Tris-Propane, sodium or potassium pyrophosphate, imidazole, PIPES, ACES, MOPS, MOPSO, BES, TES, tricine, glycylglycine, and HEPES.

In embodiments, the liquid immunogenic compositions and vaccines have a stabilizer w/v to attenuated live pathogen w/v ratio of about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1, about 51:1, about 52:1, about 53:1, about 54:1, about 55:1, about 56:1, about 57:1, about 58:1, about 59:1, about 60:1, about 61:1, about 62:1, about 63:1, about 64:1, about 65:1, about 66:1, about 67:1, about 68:1, about 69:1, or about 70:1 w/v. In embodiments, the liquid immunogenic compositions and vaccines comprise about 3% w/v of the attenuated live pathogen (e.g., PPR virus) and about 97% w/v of the stabilizer.

In embodiments, the liquid immunogenic compositions and vaccines comprise a veterinarily acceptable diluent. In embodiments, the veterinarily acceptable diluent comprises or is selected from sterile liquids such as water, oil, aqueous saline solutions, and aqueous sugar solutions (e.g. dextrose solution, glycerol solution).

In embodiments, the liquid immunogenic compositions and vaccines are packaged into vials. In embodiments, the vial is a glass vial. In embodiments, the vial is a plastic vial. Glass vials may be more effective in preventing oxidation when compared to plastic vials, and glass vials may be preferred where oxidation of the attenuated live pathogen is a concern. Plastic vials may lead to a lower cost of goods relative to glass vials, and may be preferred where oxidation of the attenuated live pathogen is of minimal concern. In embodiments, the vial is 50 cc. In embodiments, the 50 cc vial comprises about 50 mL of the liquid immunogenic composition or vaccine to minimize headspace. In embodiments, the volume of a dose in a vial can be from about 0.1 ml to about 2.0 ml. In embodiments, the volume of a dose in a vial is about 0.5 ml. In embodiments, a 50 cc vial comprising about 50 mL of liquid immunogenic composition or vaccine has about 100 doses (0.5 mL per dose). In embodiments, the vial is a sealed container. In embodiments, the vial headspace is filled with an inert gas (e.g., argon, nitrogen, helium).

The present disclosure also provides methods of immunizing an animal against a pathogen comprising administering to the animal an effective amount of a liquid immunogenic composition or vaccine according to the present disclosure.

In embodiments, the animal is a ruminant. In embodiments, the ruminant is a bovine (cattle), an ovine (sheep), and/or a caprine (goat).

In embodiments, the pathogen is peste des petits ruminants (PPR) virus, African horse sickness virus, rindepest virus, foot-and-mouth disease virus, African swine fever virus, or bluetongue virus. In embodiments, the pathogen is a PPR virus.

In embodiments, the immunogenic composition or vaccine is administered by any suitable administration method including, for example, parental administration (e.g., intramuscular, subcutaneous, intravenous, intradermal, etc.) or mucosal administration (e.g., oral, intranasal, etc). In embodiments, the volume of a dose for administration can be from about 0.1 ml to about 2.0 ml. In embodiments, the volume of a dose for administration is about 0.5 ml.

It is contemplated that the immunogenic compositions and vaccines may be administered to the animal at a single time or alternatively, two or more times over days, weeks, months, or years. In some embodiments, the immunogenic composition or vaccine is administered at least two times. In certain such embodiments, for example, the immunogenic composition or vaccine is administered twice, with the second dose (e.g., a booster) being administered at least 2 weeks after the first dose. In particular embodiments, the immunogenic composition or vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose. In the above embodiments, the first and subsequent dosages may vary, such as in amount and/or form. Often, however, the dosages are the same in amount and form. When only a single dose is administered, the amount of immunogenic composition or vaccine in that dose alone generally comprises a therapeutically effective amount of the immunogenic composition or vaccine. When, however, more than one dose is administered, the amounts of the immunogenic composition or vaccine in those doses together may constitute a therapeutically effective amount. In addition, an immunogenic composition or vaccine may be initially administered, and then a booster may be administered from 2 to 12 weeks later, as discussed above. However, subsequent administrations of the immunogenic composition or vaccine may be made on an annual (1-year) or bi-annual (2-year) basis, regardless as to whether a booster was administered or not.

EXAMPLES

Example 1: Liquid PPR

Introduction. Many viruses are sensitive to pH, osmolarity, and oxidation. If these parameters can be appropriately controlled to minimize their detrimental effects on virus degradation in a liquid formulation, then a liquid formulation may be a viable alternative to traditional freeze-dried presentations. This advantageously can eliminate the two-bottle system currently used in freeze-dried presentations.

Peste des Petits Ruminants (PPR), also known as ovine rinderpest, represents a good test case for exploring the possibility of stabilized liquid live vaccines. PPR is a contagious disease primarily affecting goats and sheep; however, camels and wild small ruminants can also be affected. PPR is currently present in North, Central, West and East Africa, the Middle East, and South Asia. It is caused by small ruminants morbillivirus in the genus Morbillivirus, and is closely related to, among others, rinderpest morbillivirus, measles morbillivirus, and canine morbillivirus (previously known as canine distemper virus). The disease is highly contagious, and can have an 80-100% mortality rate in acute cases in an epidemic setting.

Boehringer Ingelheim has commercialized a freeze-dried PPR vaccine product known as PPR-VAC (2 ml fill in 5 cc vials) that is rehydrated in the field with 50 ml of water for injection (one injection dose is 1 ml of rehydrated vaccine). There is an ongoing PPR eradication plan in Africa, and at present there is an insufficient supply of PPR doses in a freeze-dried presentation because of production capacity issues, cogs issues, and the like.

Study Design

The following study plan was devised to determine whether it was possible to sufficiently control pH, osmolarity, and oxidation in a liquid formulation to effectively minimize virus degradation such that a liquid formulation could be realized as a viable alternative to a traditional freeze-dried presentation. The study plan was also designed to investigate whether plastic vials could be used to store antigen rather than the glass vials used for the existing PPR vaccine (plastic is cheaper). The study looked at the effect of pH, vial type, and gas used on product stability.

TABLE 1 freeze-dried PPR vs. Liquid PPR vaccines

|  | Freeze-dried process | | POC liquid formulation runs |
|---|---|---|---|
| Date first production | 1998 | | 2019 |
| AI composition | 50% virus harvest/50% stab 30 | | |
| Formulation | Currently | Final future formulation (to be confirmed) | 3% AI + 97% Stab 30 |
|  | Formulation by volume: 98% AI 2% stab maltose (1733258A10) | =Formulation by titer: Conventional Target = 5 log10 TCID50/mL TOR: Target = 6 log10 TCID50/mL Proportion of AI will differ depending on AI titer at harvest. Addition of: Media (MEM) to dilute the AI Stab 30 to maintain 50% in the final product 2% maltose | |
| Vial used | Glass 5/7 mL. Glass of type I or II, European Pharmacopeia or plastic vial (to be defined) | | Glass or PE 50 mL |
| Volume vaccine (mL) | 2.2 | | 50 (up to the maximum) |
| Freeze-drying process | 48 h (Freezing 3.5 h, P1 31 h, P2 13.5 h) | | 0 h |
| Average freeze-dried loss (log 10) | 0.4 | | 0 |
| Average loss 1M 5° C. (log 10) | 0 | | 0.6 |

TABLE 2

Stabilizer Composition for freeze-dried and liquid vaccines

| | Stab 30 (freeze-dried) | 1733258A10(liquid) |
|---|---|---|
| E-Saccharose CODEX BD (E-sucrose) | 10% | 10% |
| Lactalbumin hydrolysate irradiated | 5% | 5% |
| E-Glutamate sodium 1H2O POT | 1.25% | 1.25% |
| Maltose | 0 | 40% |
| Sodium hydroxide 5N | pH adjustment (target = 7.1) | pH adjustment (target = 7.1) |

TABLE 3

Conditions tested for PPR proof of concept (POC) liquid formulation

| Condition | pH | Vial | Stab 30 | Gas |
|---|---|---|---|---|
| 1 | 6.5 | Glass | QS50 | No |
| 2 | | PP | QS50 | No |
| 3 | 7 | Glass | QS50 | No |
| 4 | | PP | QS50 | No |
| 5 | 7.5 | Glass | QS50 | No |
| 6 | | PP | QS50 | No |
| 7 | 7 | Glass | QS 2.2 | Nitrogen |

In the study, the active ingredient (AI) used was PILOTD7 (titer=6.0 log 10 TCID50/mL). Each vial of liquid PPR vaccine was filled to the maximum (~50 mL, 100 doses) to minimize headspace, thereby minimizing the risk of oxidation. In test condition seven, the headspace was filled with nitrogen before stoppering the vials (to further avoid oxidation and evaluate the impact of osmolarity alone).

Osmolarity was evaluated as follows: the current freeze-dried vaccine is 2 ml in 5 CC vials (for a 50 doses vaccine). The direct 50 doses liquid vaccine used the same amount of virus as the freeze-dried vaccine, and the virus was diluted to 50 mL in stabilizer (which provides a high osmolarity). An osmolarity reference was created by formulating a 2 ml liquid formulation in a 5 CC vial (same amount of virus, but lower amount of stabilizer).

Results

FIG. 1 graphically depicts the stability data of Table 4.

Analysis

Nitrogen inerting does not show a benefit. Glass bottles gave better results than plastic bottles, confirming the importance of oxidation as plastic bottles are not oxygen proof. The lower pH gives better results. The 50 ml fill/50 CC bottle seems to give better results than 2 ml/5 CC (likely confirming the role of high concentration of stabilizer, and the role of osmolarity).

The invention claimed is:

1. A liquid immunogenic composition comprising:
an attenuated live peste des petits ruminants (PPR) virus; and
a stabilizer comprising about 1% to about 20% w/v sucrose, about 0.5% to about 10% w/v irradiated lactalbumin hydrolysate, about 0.5% to about 5% w/v glutamate sodium, and about 10% to about 80% w/v maltose, wherein the liquid immunogenic composition is not lyophilized.

2. The liquid immunogenic composition of claim 1 wherein the stabilizer comprises about 10% w/v of the sucrose.

3. The liquid immunogenic composition of claim 1, wherein the stabilizer comprises about 5% w/v of the irradiated lactalbumin hydrolysate.

4. The liquid immunogenic composition of claim 1, wherein the stabilizer comprises about 1.25% w/v of the glutamate sodium.

5. The liquid immunogenic composition of claim 1, wherein the stabilizer comprises about 40% w/v of the maltose.

6. The liquid immunogenic composition of claim 1, wherein the pH of the liquid immunogenic composition is in the range of about 6.5 to about 7.5.

7. The liquid immunogenic composition of claim 1, wherein the pH of the liquid immunogenic composition is about 7.1.

8. The liquid immunogenic composition of claim 1, wherein the attenuated live virus is about 3% w/v of the liquid immunogenic composition, and wherein the stabilizer is about 97% w/v of the liquid immunogenic composition.

9. The liquid immunogenic composition of claim 1, wherein the liquid immunogenic composition is a vaccine.

10. A glass vial comprising the liquid immunogenic composition of claim 1.

11. The glass vial of claim 10, wherein the vial is 50 cc.

TABLE 4

Stability results at 1, 2, 3, and 8 months at 5° C.

| | | Timeline | | | | | Titer loss after 8 M 5° C. (log10) |
|---|---|---|---|---|---|---|---|
| Batch number | Condition | T0 (1 week 5° C.) | 1 M 5° C. | 2 M 5° C. | 3 M 5° C. | 8 M 5° C. | |
| | | Average (TCID50/flacon 100D) | | | | | |
| 19PPR8C51 | pH 6.5 glass vial 50 mL | 6.28 | 6.05 | 5.70 | 5.70 | 5.80 | 0.48 |
| 19PPR8C52 | pH 6.5 PP vial 50 mL | 6.32 | 5.68 | 5.57 | 5.60 | 5.70 | 0.62 |
| 19PPR8C61 | pH 7 glass vial 50 mL | 6.38 | 5.85 | 5.77 | 5.60 | 5.50 | 0.88 |
| 19PPR8C62 | pH 7 PP vial 50 mL | 6.42 | 5.72 | 5.70 | 5.53 | 5.00 | 1.42 |
| 19PPR8C71 | pH 7.5 glass vial 50 mL | 6.18 | 5.52 | 5.60 | 5.33 | 4.50 | 1.68 |
| 19PPR8C72 | pH 7.5 PP vial 50 mL | 6.25 | 5.82 | 5.60 | 5.20 | 4.90 | 1.35 |
| 19PPR8C81 | pH 7 glass vial 2.2 mL + inerteazote | 6.14 | 5.51 | 4.34 | 2.98 | <1.9 | >4.24 |

12. The glass vial of claim 10, wherein the glass vial comprises about 50 mL of the liquid immunogenic composition.

13. A method of immunizing an animal against PPR virus, comprising:
   administering to the animal an effective amount of the liquid immunogenic composition of claim 1.

14. The method of claim 13, wherein the animal is a ruminant, and wherein the effective amount comprises about 0.5 mL of the liquid immunogenic composition.

15. The method of claim 13, wherein the stabilizer comprises about 10% w/v sucrose, about 5% w/v irradiated lactalbumin hydrolysate, about 1.25% w/v glutamate sodium, and about 40% w/v maltose.

16. The liquid immunogenic composition of claim 1, wherein the composition is in a ready to use form and packaged into a sealed container.

17. The method of claim 14, wherein the ruminant is a bovine, an ovine or a caprine.

* * * * *